(12) United States Patent
Steer et al.

(10) Patent No.: US 6,537,261 B1
(45) Date of Patent: Mar. 25, 2003

(54) OSTOMY COUPLING

(75) Inventors: Peter L. Steer, Sussex (GB); Keith G. M. Hollands, W. Sussex (GB); Timothy K. Thorndale, Surrey (GB)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/467,424

(22) Filed: Dec. 20, 1999

(51) Int. Cl.⁷ .................................................. A61F 5/44
(52) U.S. Cl. ........................................................ 604/342
(58) Field of Search ................................ 604/317, 322, 604/327, 332, 337, 338, 339, 341, 342, 343, 344

(56) References Cited

U.S. PATENT DOCUMENTS

| | | | | |
|---|---|---|---|---|
| 5,302,173 A | * | 4/1994 | Steer | 604/338 |
| 5,496,297 A | * | 3/1996 | Olsen | 604/339 |
| 5,709,674 A | * | 1/1998 | Steer | 604/342 |
| 5,814,033 A | * | 9/1998 | Edwrads | 604/342 |
| 5,947,947 A | * | 9/1999 | Leise, Jr. et al. | 604/338 |
| 6,093,276 A | * | 7/2000 | Leise, Jr. et al. | 156/249 |
| 6,106,507 A | * | 8/2000 | Botten et al. | 604/338 |
| 6,197,010 B1 | * | 3/2001 | Leise, Jr. et al. | 604/338 |

FOREIGN PATENT DOCUMENTS

GB    2299510    * 9/1996

* cited by examiner

*Primary Examiner*—Kim M. Lewis
(74) *Attorney, Agent, or Firm*—Stuart E. Krieger

(57) ABSTRACT

A flush fit ostomy coupling (110) includes a bagside coupling member (114) with a front flange (116) from which an outer wall (22) depends rearwardly. A channel is formed between the outer wall and an inner wall (124) supported by the outer wall.

The bodyside coupling member (112) carries sealing means in form of first and second substantially radially projecting sealing fins (152). The sealing fins are able to deflect to form a cylindrical band seal against one wall (122) of the channel. The opposite wall (124) of the channel forms an interlock with the bodyside coupling member.

The radial sealing fin may be used with other types of ostomy coupling. Also, the flush fit design may employ other types of seal.

12 Claims, 13 Drawing Sheets

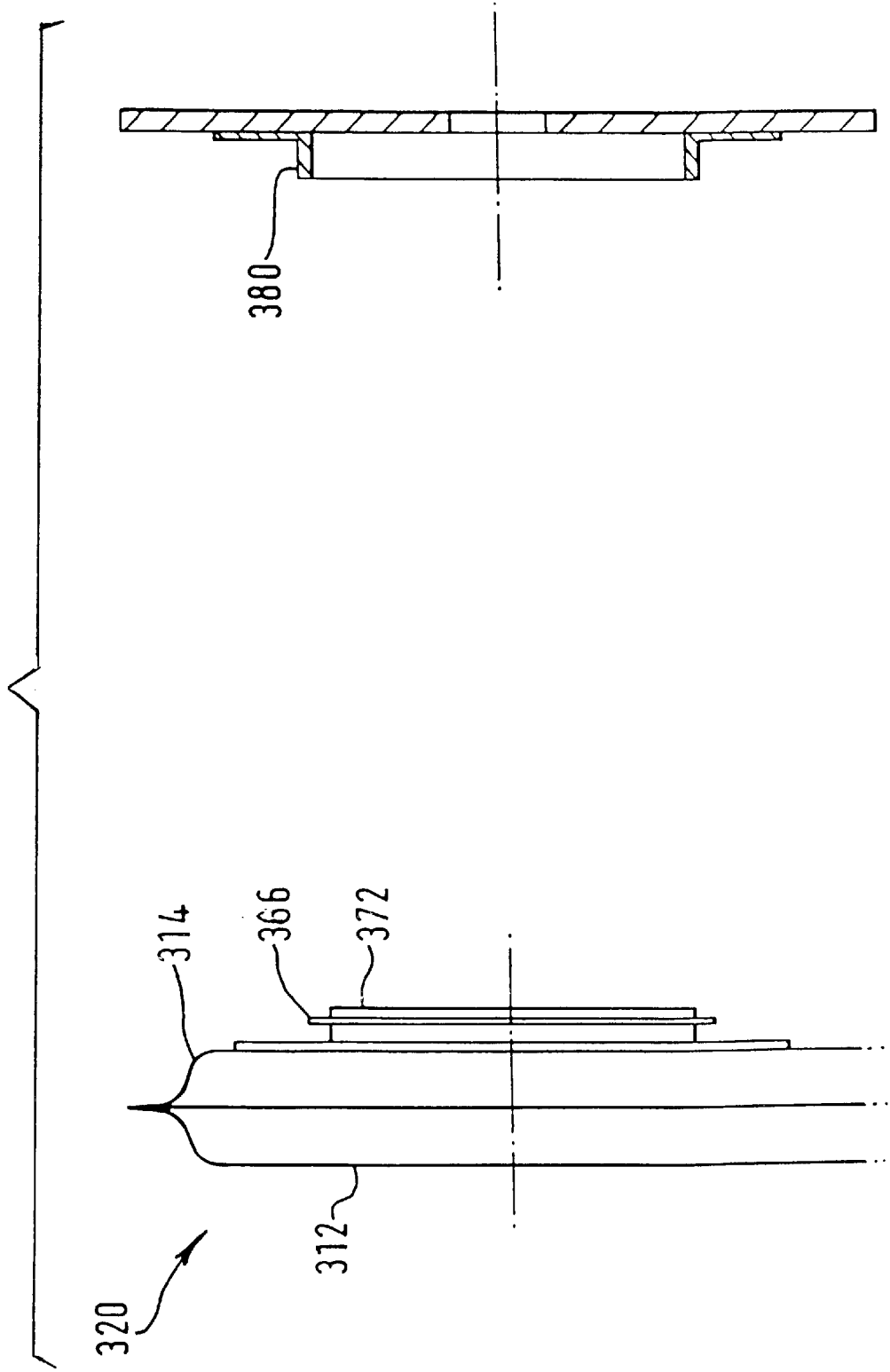

OSTOMY COUPLING

This invention relates to the field of ostomy products, and in particular to a coupling for releasably attaching an ostomy pouch to a pad or wafer worn on the body. The term "ostomy" is intended to be interpreted broadly, and includes colostomy, urostomy and ileostomy.

FLUSH FIT COUPLING

In one form, the invention relates to a so-called two-piece coupling consisting substantially of only two coupling members, one for the bag side of the coupling and the other for the body side.

There are many different designs of two-piece coupling. Typically, the mutually engaging regions of the bodyside and bagside coupling members result in a deadspace being created between the pouch and the body pad or wafer; in other words, the pouch is held away from the pad by a distance corresponding to the "height" of the coupling. Generally, it is desired that the coupling members have a low profile, so as to keep the deadspace to a minimum.

A coupling has been proposed in U.S. Pat No. 4,872,869 in which the ostomy pouch is a flush fit, or almost a flush fit, against the body pad. Such an arrangement is referred to herein as a flush-fit coupling.

Broadly speaking, in a first aspect, the invention provides a flush-fit coupling including a bagside coupling member and a bodyside coupling member securable together.

The coupling preferably has one or more of the following features:

1. The bagside coupling member includes an inner first wall, and an outer second wall defining a connection channel therebetween, and of the first and second walls, one of said walls comprises or carries a locking projection facing the interior of the channel, the surface of the other wall facing the channel being a generally smooth sealing surface.

Such an arrangement can provide significant technical advantages, over the prior art.

In particular, the coupling described in the aforementioned U.S. Pat. No. 4,872,869, relies on locking profiles on both of the cylindrical walls defining the channel of the bagside coupling member. The locking profiles act in combination with a central rib, to trap the connecting part of the bodyside member in the channel. The interlocking regions have a dual function in providing a seal and a secure fastening.

However, in developing the present invention, it was appreciated that a user may have severe problems trying to release the aforementioned prior art coupling to separate an ostomy pouch from the body part after use. The problem arises because the connecting part of the bodyside member is interlocked by both the channel walls, and is also expanded by the rib in the channel. This can make it virtually impossible to withdraw the connecting part from the channel, without twisting or deforming the channel somehow. The above problem is magnified by the coupling being recessed inside the pouch. Even flexing of the front flange of the bagside coupling member would provide little assistance to releasing both channel walls, since the recessed design of the coupling member means that the front flange is not coupled directly to the base of the channel.

Such a coupling thus requires considerable dexterity to release, and would provide problems for many ostomates, who are often elderly and may not have much strength in their fingers.

However, with the present invention, by providing different wall portions to provide a sealing function (i.e. either the inner, first wall, or the outer, second wall) and a locking function (i.e. either the outer, second wall, or the inner, first wall, respectively), many of the above problems can be avoided. The coupling can be made much easier to release without having to weaken the seal, and without having to weaken the security of the coupling.

Preferably, the wall carrying the locking projection carries a plurality of locking projections. For example, the locking projections may be spaced apart angularly.

In a closely related specific aspect, the invention provides a flush fit ostomy coupling, comprising:

a bagside coupling member comprising an inner first wall and an outer second wall defining a channel therebetween, a mounting flange extending outwardly from the second wall at the mouth of the channel, one of the first and second walls comprising at least one locking projection facing the first wall;

a bodyside coupling member comprising a projection which, in use, is received within the channel of the bagside coupling member, the projection including a formation for interlocking engagement with the locking projection of one of said walls of the bagside coupling member, and a deflectable seal for non-interlocking engagement with the other wall of the bagside coupling member.

2. The bagside coupling member is secured to an ostomy pouch comprising first and second pouch walls and having an entrance aperture in the first pouch wall, the bagside coupling member being carried by the first pouch wall at the aperture, at least a portion of the bagside coupling member extending inside the pouch. Anti-sealing means is provided for preventing in use sealing between a portion of the bagside coupling member and the interior face of the second pouch wall.

This feature of the invention can avoid the potential problem of, for example, the front wall of the pouch opposite the coupling member tending to stick to the coupling member when the pouch is first used. This effect is similar to the problem of pancaking in which the front and rear walls of the pouch can sometimes stick together, and obstruct the entry of body waste into the pouch. The use of a coupling member extending at least partly inside the pouch can actually reduce the effect of direct pancaking between the front and rear walls at the aperture (by holding the walls apart to some extent), but there is then the potential problem of the pouch wall tending to seal or stick to the coupling member, which again would obstruct entry of body waste into the pouch. However, by using anti-sealing means in accordance with this aspect of the invention, this potential problem can be avoided or at least reduced.

The anti-sealing means may comprise a non-planar surface of the coupling member, for example, one or more projections or recesses, or an undulating surface, to promote channels or spaces being created between the coupling member surface and the opposing face of the pouch wall. Alternatively, the anti-sealing means may comprise a non-stick coating carried by the coupling member and/or by the pouch wall.

In a closely related specific aspect, the invention provides a bagside coupling member for a flush fit coupling, the bagside coupling member comprising a coupling channel, and anti-sealing means on the rear surface of the channel.

3. The bagside coupling member is carried by an ostomy pouch comprising first and second pouch walls, there being an entrance aperture in the first pouch wall, the bagside coupling member being carried by the first pouch wall at the aperture, at least a portion of the bagside coupling member extending inside the pouch, and a surface of the bagside coupling member confronting the second wall being substantially non-planar.

In addition to any non-sealing effect, this feature can improve the extent to which a user is able to feel by hand the profile of coupling member through the pouch wall material, to enable the user better to position his hands during fitting of the pouch to the body, and during removal of the pouch from the body. During the development of the present invention, it has been appreciated that the recessed nature of the "flush-fit" bagside coupling member results in the coupling being considerably more hidden from the user's view. This loss of visibility can make the coupling more difficult to fit and remove. Therefore, improving the tactility of the coupling through the second pouch wall can compensate for loss of visibility of the coupling member.

In one preferred embodiment, the surface comprises a plurality of spaced apart projections, for example, small domes. In another embodiment, the surface comprises an annular projection.

In a closely related specific aspect, the invention provides a bagside coupling member for a flush fit coupling, the bagside coupling member comprising a coupling channel, a surface of the coupling member directed away from the open mouth of the channel being substantially non-planar to enable said surface to be felt by hand through a pouch wall.

4. The bagside coupling member comprises a channel defined by first and second wall portions and a base portion between the first and second wall portions, at least one of said portions comprising a region of reduced thickness.

With this aspect of the invention, the region of reduced thickness provides a natural hinging effect to enhance the extent to which the channel can open when the bagside coupling member is assembled to, or is separated from, a body-side coupling member. During the development of this aspect of the invention, it was appreciated that the concept of a recessed channel for a "flush fit" bagside coupling member is more problematic than an external coupling member, because as explained above, in a recessed design the channel is supported around its mouth rather than around its base. This means that the channel is stiffer, and is not free to "open" in the same way as a channel supported at its base. Moreover, in a recessed design, the channel is inaccessible, and it is generally more difficult to flex the recessed channel when the bag-side and body-side coupling members are to be released.

However, by using this aspect of the invention to enhance the extent to which the channel can open, the above problems can be substantially alleviated.

Preferably, the first and/or the second wall portion of the channel comprises a region of reduced thickness. In some preferred embodiments, the first and/or the second wall portion is tapered to thin towards the base portion. Additionally, or alternatively, the base portion may include one or more recesses which can enhance the flexibility of the channel base.

5. The bagside coupling member is secured to an ostomy pouch comprising first and second walls, there being an entrance aperture in the first wall, and the bagside coupling member being carried by the first wall at the aperture, the bagside coupling member comprising a channel at least a portion of which extends into the interior of the pouch, the channel being defined by generally concentric outer and inner walls, wherein the inner wall projects through the aperture from the interior of the pouch to the exterior, and the inner wall is proud of the outer wall.

With this feature, there is a step in the relative heights of the inner and outer walls.

Preferably, the outer wall carries or comprises at least one locking projection. Preferably, the inner wall provides a planar sealing surface.

This feature of the invention can provide a recessed coupling with a relatively large wall surface for forming a seal with a body-side coupling member, without increasing substantially the depth of the coupling member within the interior of the pouch. It will be appreciated that it would be undesirable to have too great a depth of coupling within the pouch, as this would cause the pouch to bulge in the region of the coupling.

In a closely related specific aspect, the invention provides a bag-side coupling member for a flush fit coupling, the bagside coupling member comprising a mounting flange, a first wall portion depending from the flange, a second wall portion concentric with the first wall portion and defining therewith a connection channel, the second wall portion being proud of the first wall portion.

Coupling Seal

Another aspect of the invention relates to sealing means for forming a seal between a bagside coupling member and a bodyside coupling member. This aspect of the invention is applicable to a flush-fit coupling as well as to a non-flush-fit coupling. This aspect is also applicable to two-piece couplings, and to multi-piece couplings. It is also applicable to couplings which are secured together mechanically as well as to adhesive couplings.

There are many different designs of seal. A particularly successful design used in a mechanical interlock coupling is illustrated for example in GB 1 571 657. This design includes a cylindrical rib which is received within an annular channel. The outer edge of the rib has a profile which interlocks with the inner edge of the outer channel wall to hold the coupling parts together in use. The rib also has an inwardly inclined frusto conical wiper which forms a seal against the inner wall of the channel.

The above design has proven to be extremely reliable in practice. The wiper is able to deform sufficiently to accommodate tolerance variations and relative movement of the coupling members. However, the minimum profile "height" of the coupling which can be achieved is limited by the presence of the wiper, which must have at least a certain minimum length. The wiper cannot be shortened significantly, as this would affect the seal integrity and the ability to accommodate size variations.

In general, a low profile is desirable as this reduces the dead-gap between the ostomy pouch and the person's body (for non-flush-fit couplings), and also reduces the prominence of the pouch (for flush-fit and non-flush-fit couplings).

Reference is also made to GB-A-2 157 567 which discloses an adhesive coupling in which an inwardly extending lip of the ostomy pouch material stretches to form a tight fit around the chute of a body side member. This design suffers from manufacturing problems in that it relies on forming an accurately sized opening in the pouch wall. Moreover, it relies on accurate positioning of the aperture and of the bagside coupling member around the aperture. Such tolerances require very expensive manufacturing machinery for large scale production. A further problem is that the seal relies on the characteristics of the pouch material, which might not be ideal to form a resilient seal.

This aspect of the invention has been devised bearing the above in mind.

In contrast to the prior art, the present aspect of the present invention is to provide a closed-loop shape sealing fin projecting generally laterally (at least in one operative condition, for example, a non-deformed condition) from a wall or chute portion of a coupling member, the sealing fin being of resiliently flexible material and being distinct from the pouch wall.

When the wall or chute carrying the fin is on the bag-side coupling member, preferably the fin extends from a position which is offset axially, at least to some extent, relative to the joint between the coupling member and the pouch wall material.

This aspect of the invention can provide significant advantages over the prior art arrangement as follows:

(a) the seal performance is not limited by the accuracy of the position of the coupling member relative to the stoma aperture in the pouch wall, nor is it limited by the exact size of the stoma aperture in the pouch wall. This enables conventional assembly machines which have modest tolerances to be used for mounting the coupling member on the pouch, and for punching the stoma aperture in the pouch wall material.

(b) The seal performance is not limited by the specific properties of the pouch wall material;

(c) The seal fin can be made of relatively soft resilient material. This can provide an excellent seal with only low assembly (insertion) forces being required;

(d) A coupling member can be constructed which has a very low profile. For example, compared to integral frusto-conical deflectable wipers, a smaller insertion depth might be achieved while still obtaining a reliable seal.

(e) The flexibility of the fin can enable wider dimensional tolerances to be accommodated than in some prior art designs, without reducing seal performance.

Preferably, the body-side and bag-side coupling members are configured such that the fin projecting from the chute on the member engages against the surface of a second chute wall (or cylindrical wall) on the other coupling member. Preferably, the chutes fit one inside the other when the coupling members are assembled together.

The fin may be provided on the bagside coupling member, or on the bodyside coupling member.

The coupling member may include one such fin, or two fins, or more fins, as desired.

The coupling member including the fin may be produced by a variety of techniques. Examples include:

(a) multi-shot (e.g. two shot) moulding;

(b) insert injection moulding (similar to multi-shot moulding, but with this technique the plastics material is allowed to set before the next plastics is moulded);

(c) fabrication using a plurality of pre-formed components which are in turn assembled to form a finished item, retained in its assembled condition by mechanical interlocking, adhesive or welding; or (d) integrally moulding the member integrally of a flexible polymer, for example, using injection moulding.

Another related aspect of the present invention is to use one or more sealing elements carried by, and extending or projecting generally radially from, a first wall of the coupling, the one or more sealing elements being formed from a plastics material which is softer than the material of the first wall.

In a preferred form, the one or more sealing elements extend or project generally radially at least in an undeflected state (for example, when the coupling members are separated).

The combination of a generally radially extending or projecting seal, and the seal material being of generally softer material then the or a structural part of the coupling, can enable a low coupling profile to be achieved without impairing the characteristics of the seal.

Such a design is especially suitable for a two piece mechanical interlock coupling, but it is also suitable for use in many other types of coupling, for example, types including a locking ring, or types secured together by adhesive.

Preferably, the one or more sealing elements are integrally moulded with the first wall. For example an insertion injection moulding process, or a multi-shot moulding process may be used. Reference is made to the techniques described in GB-A-2 323 285.

Preferably, in either of the above aspects, at least one sealing element or fin forms a seal spread axially over a cylindrical band or region, rather than forming a so-called "point seal" at only one axial point. By spreading the seal axially, the seal is better able to withstand relative movement or distortion of the coupling members without loss of seal integrity.

Preferably, at least one sealing element or fin is in the form of a deflectable wiper which will deflect to some extent upon contact with the opposite coupling member. Such deflection can ensure that the sealing element bears on the opposite surface with a modest but sufficient force to achieve a seal, and preferably also can enable the above larger area (cylindrical band) seal to be achieved.

Preferably, at least one sealing element or fin is tapered towards its free edge.

Preferably, at least one sealing element or fin is distinct from the material of the ostomy pouch. Preferably, the sealing element lies in a plane which is offset from the plane of the ostomy pouch material.

If desired the one or more sealing elements could project radially inwardly from the first wall of the coupling member. However, in a particularly preferred form of the invention, the one or more sealing elements project radially outwardly from a cylindrical rib of the coupling member. Such a design can facilitate easier moulding when a plurality of sealing elements are used.

In a closely related aspect, the invention provides a first coupling member for use in a two piece ostomy coupling of the type including first and second coupling members releasably securable together by a mechanical interlock, the first coupling member comprising a first portion of a first relatively rigid plastics material integrally moulded with a second portion of a second relatively soft plastics material, the first portion comprising a locking profile for forming a mechanical interlock with the second coupling member, and the second portion comprising a sealing element.

In a closely related aspect, the invention provides a first coupling member for use in a coupling of the type including first and second coupling members which are mechanically securable together, the first coupling member comprising a least one generally annular sealing fin which projects generally radially from a cylindrical wall, the fin tapering in thickness towards its free edge.

The above aspects of the invention may be used independently, but further advantages may be achieved by using tow or more aspects in combination.

DESCRIPTION OF THE DRAWINGS

Embodiments of the invention are now described by way of example only, with reference to the accompanying drawings, in which:

FIG. 21 is a partial schematic view of an alternative embodiment of adhesive ostomy coupling.

DESCRIPTION OF PREFERRED EMBODIMENTS

Figure 1:
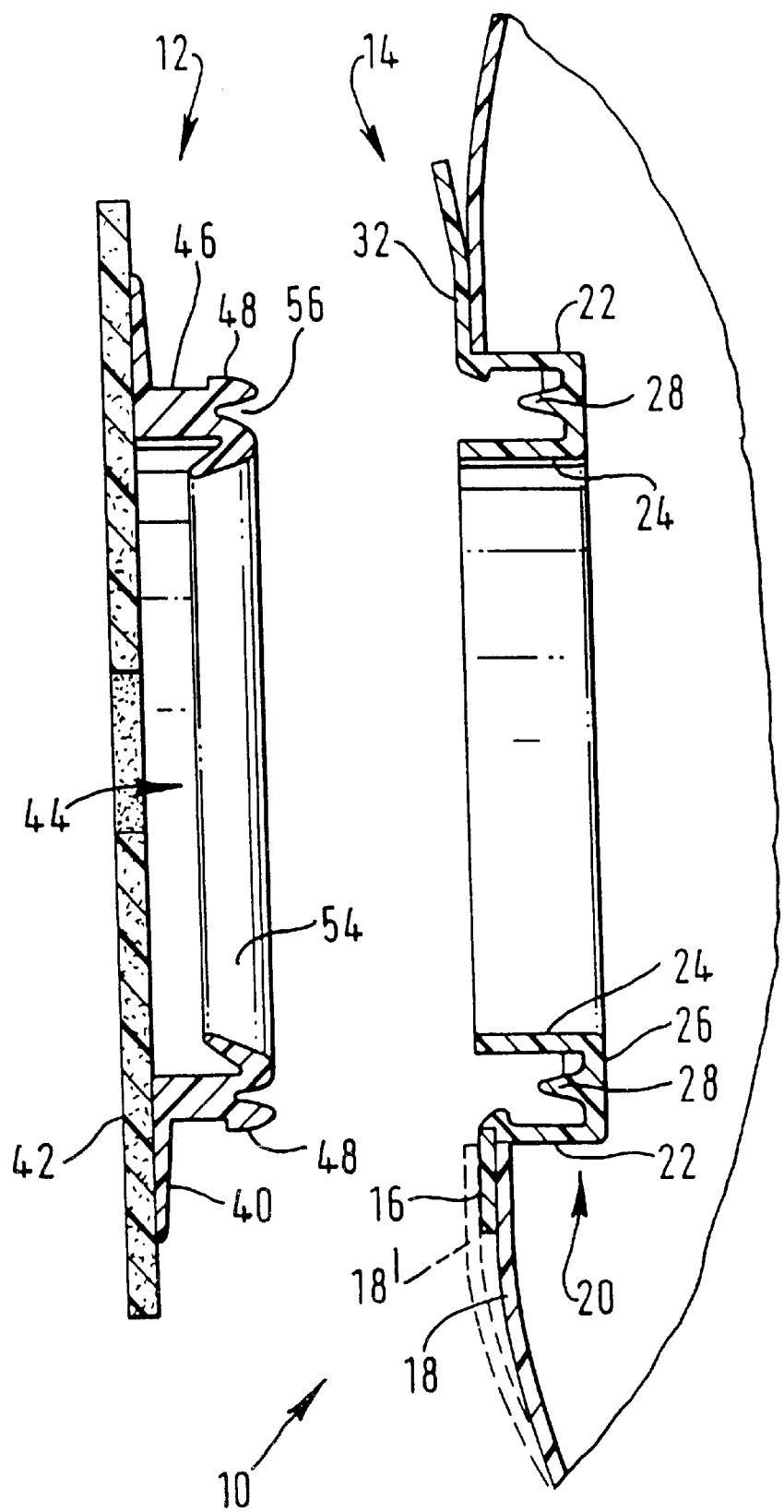
FIG. 1 is a schematic sectional view showing the bodyside and bagside members of a first embodiment of ostomy coupling.
Figure 2:
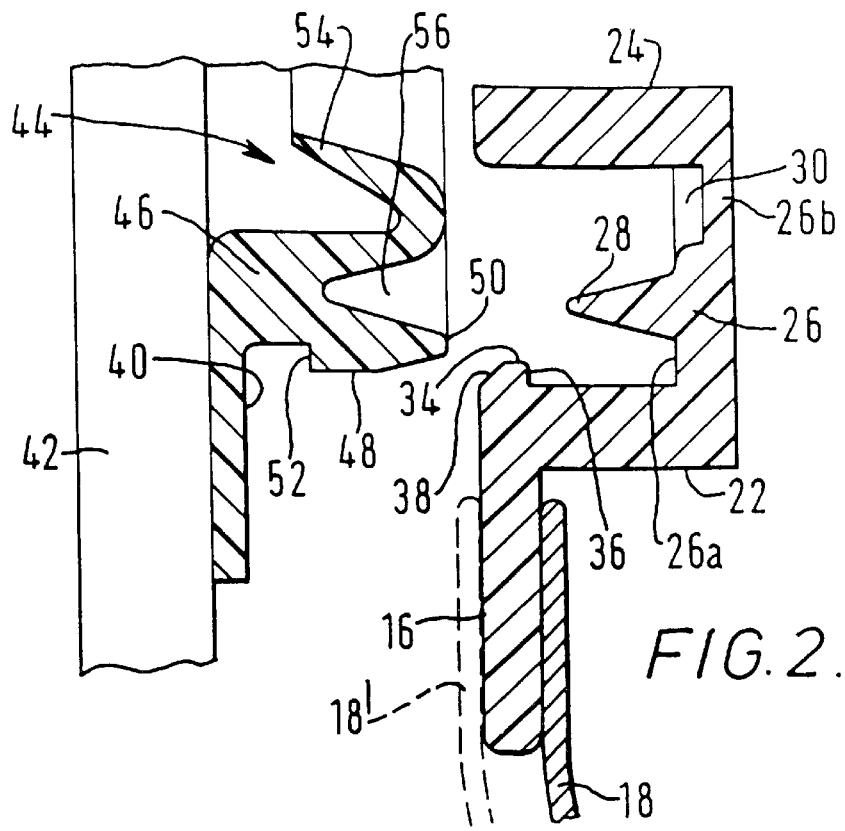
FIG. 2 is an enlarged schematic section showing a detail of the coupling members of FIG. 1.
Figure 3:
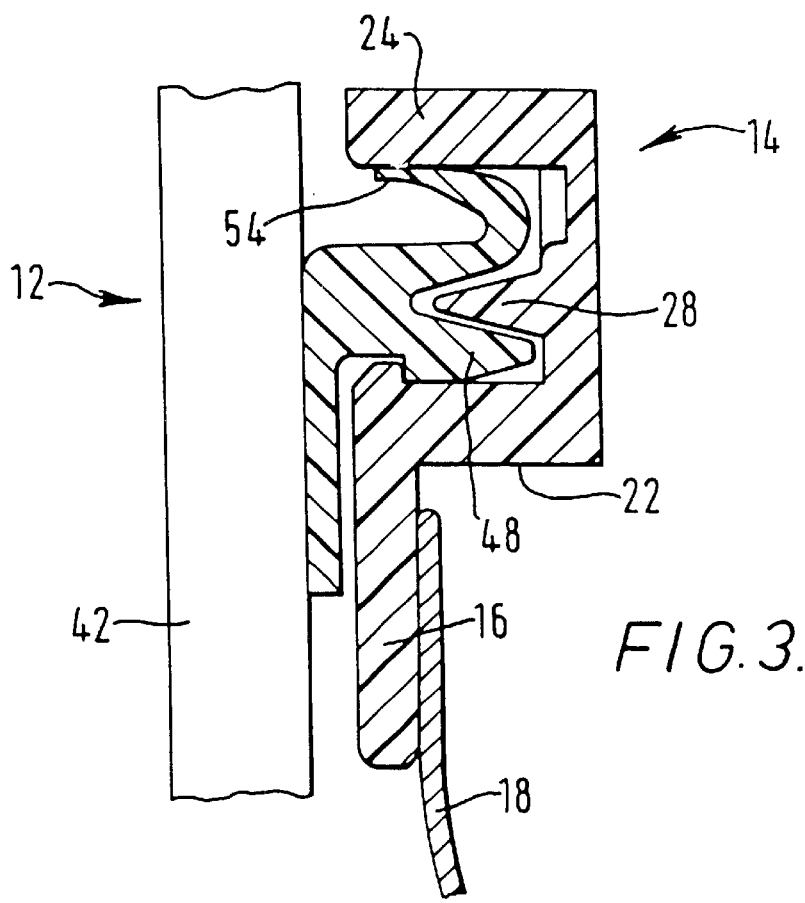
FIG. 3 is a view similar to FIG. 2, but showing the coupling members in the assembled condition.
Figure 4:
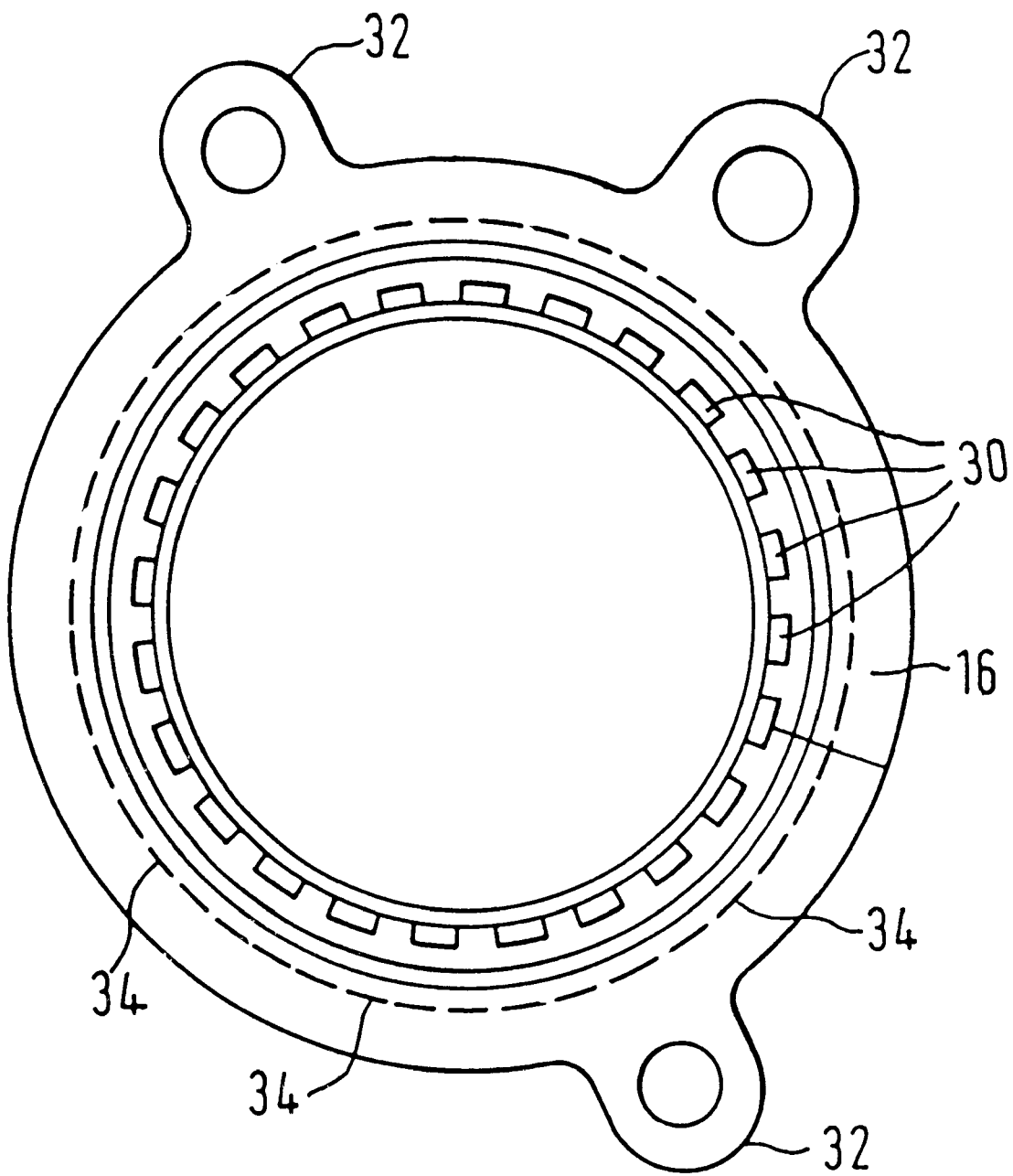
FIG. 4 is a front view of the bagside member of the first embodiment.
Figure 6:
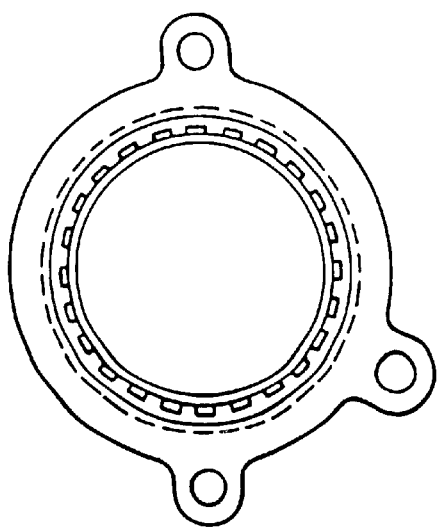
FIG. 6 is a front view of the bagside coupling member of FIG. 5.
Figure 5:
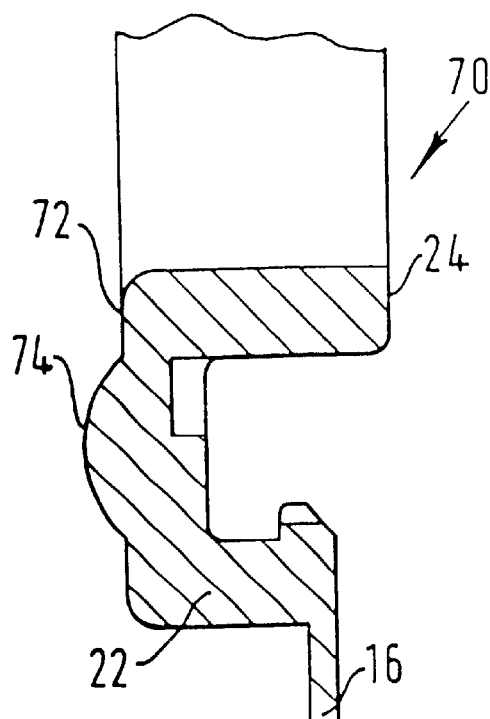
FIG. 5 is a partial schematic view showing a modified form of bagside coupling member.
Figure 7:
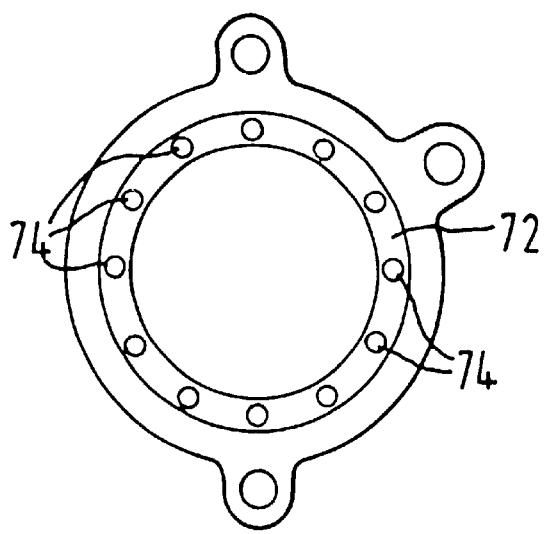
FIG. 7 is a rear view of the bagside coupling member of FIG. 5.

Referring to FIGS. 1 to 4 of the drawings, a two-piece ostomy coupling 10 consists generally of a bodyside coupling member 12 and a bagside coupling member 14.

The bagside member 14 comprises a flange 16 which in this embodiment is attached to the outer face of a pouch wall 18 by gluing, welding, or any other suitable fixing. However, as explained further below, the flange 16 could be attached to the inner face of wall 18 if desired. The flange 16 has a stomal aperture which is aligned with a corresponding aperture 20 in the pouch wall 18. Depending from the inner edge of the flange 16 is an outer cylindrical wall 22 which extends rearwardly into the pouch, and positioned concentrically inside the outer wall 22 is a cylindrical inner wall 24. The inner wall 24 and the outer wall 22 define a connection channel, and the walls are coupled to each other by a channel floor 26. A locating rib 28 projects from the floor 26 to a lesser extent than the inner and outer walls. In this embodiment, the locating rib 28 has a generally tapered shape, but it will be appreciated from later description that other shapes of rib 28 may be used as desired.

A number of radially projecting belt tabs and/or pull tabs 32 are provided as extensions of the front flange 16, to enable the flange 16 to be gripped, as described later.

The floor 26 of the channel includes a radially outer portion 26a between the rib 28 and the outer wall 22, and a second radially inner portion 26b between the rib 28 and the inner wall 24. The radially inner portion 26b includes a plurality of, in this embodiment regularly spaced, recesses 30 for facilitating moulding of the coupling member as described in WO-A-93/23229 and also described briefly below.

The outer wall 22 carries, on its inner face, a plurality of spaced apart projections 34. These serve to form an interlock with a corresponding formation of the body side member. Each projection 34 includes a generally flat or undercut rear surface 36, and an upper ramp surface 38.

As described in WO-A-93/23229, during production of the bag side coupling member, the spacing between the projections 34 permits the portions of the moulding tool (not shown) under the projections 34 to be removed from inside the channel by rotating the tool relative to the coupling member (or vica versa) until the moulding tool portions can be withdrawn through the spaces. The recesses permit keying engagement with the moulded member to achieve the controlled rotation.

The bodyside member 12 comprises an annular flange 40 which is attached to an adhesive "wafer" or pad 42 for attachment to a person's skin. The pad 42 may be made of Stomadhesive or other known skin adhesives; such adhesives are well known to the skilled man and so are not described further here.

The flange 40 includes a stomal aperture 44 bounded by a generally annular formation 46 configured to fit within the channel of the bag side member. The formation 46 includes a radially outer locking rib 48 for fitting between the outer wall 22 and the locating rib 28 of the bag side member 14. The locking rib 48 includes a generally rounded or tapered tip 50, and a stepped or undercut locking formation 52 for co-operating with the projections 34. The formation also includes a radially inwardly directed seal wiper 54 for forming a seal against the radially outer face of the inner wall 24. The wiper 54 is at least partly deformable or deflectable, and is bent over at its upper end and tapers towards its tip. A generally annular groove 56 between the wiper 54 and the locking rib 48 is configured to co-operate with the locating rib 28 as described further below.

To assemble the coupling members, the bag side member 14 is positioned against the body side member 12, and is pressed against the body side member. Under quite mild pressure, the locking rib 48 is able to pass over the ramp surfaces 38 of the projections 34, until the projections snap into engagement against the locking formation 52 of the locking rib 48. During such assembly, the engagement will not normally occur simultaneously all around the coupling circumference. Rather, engagement will tend to begin in one annular region, and then progress around the coupling until a complete circle is achieved. Such engagement can result in the bag side member tilting relative to the axis of the body side member. In the present embodiment, the locating rib 28 and the groove 56 act to prevent such tilting, and also ensure that the bag side member is accurately centred on the body side member 12. It will be appreciated that, since there is no interlock between the wiper 54 and the inner wall 24, accurate centring is important to enable the seal wiper 54 to engage properly against the smooth surface of the inner wall 24 to form a reliable seal all around the wall.

The relative shapes of the locating rib 26 and the groove 56 can be varied as desired, but the illustrated smoothly tapered shape is currently preferred for ease of moulding and for optimum guidance during assembly of the coupling members.

In the assembled condition, (illustrated in FIG. 3), the pouch is generally flush against the body side pad 42, and there is very little wasted deadspace between the pouch and the body side pad. In the illustrated preferred embodiment, the rib 28 is dimensioned relative to the groove 56 such that the rib 28 does not tend to force the locking rib 48 and the wiper 54 apart. Nevertheless, the engagement between the locking projections 34 and the undercut 52 of the locking rib 48 provides a reliable fastening to prevent accidental release of the pouch.

To separate the engaged coupling members, the bag side member 14 is peeled away from the body side member 12, for example, by grasping and pulling one of the tabs 32. The plastics material of the outer wall 22 of the bagside member 14 is able to deform sufficiently to allow release with a modest separation force being applied. In particular, no deformation of the inner wall 24 of the bagside member 14 is required, because the inner wall does not interlock with the body side member, and the body side formation 46 is not trapped by that wall.

In the illustrated embodiment, the flange 16 of the bag side coupling member 14 is secured to the exterior face of the pouch wall 18. However, if desired, the flange could be secured to the interior surface of the pouch wall (i.e. to pouch wall 18' depicted in phantom).

The coupling members are each preferably integrally moulded. Suitable plastics materials include, for example, low and high density polyethylene, thermoplastic elastomers (TPE), polyvinyl chloride (PVC), acetyl plastics, ABS, polyamides, and combinations of any of these. For example, different plastics might be used for the two coupling members to give one a generally hard or rigid characteristic, and the other a more pliant characteristic. The materials used may also depend on the weldability of the material to, for example, a pouch wall for the bagside coupling member, and to the adhesive wafer laminate for the bodyside coupling member.

FIGS. 5–8 illustrate a modified form of bagside coupling member 70. This is similar to the bagside coupling member 14 of the first embodiment, except for the following features:

(a) The locating rib 28 of the first embodiment is omitted, which means that the complementary formation (46) of the bodyside coupling member can be simplified by removing the annular groove (56). It will be appreciated that the locating rib 28 and groove 56 could still be included, if desired.

(b) The inner wall 24 is axially longer than the outer wall 22, and projects proud of the flange 16. Depending on the thickness of the pouch wall material or materials, and also depending on how the flange 16 is secured to the pouch wall, the inner wall 24 may project to be proud of the pouch wall.

The increased length of the inner wall 24 can improve the ease of aligning the bagside and bodyside coupling members for assembly. It can also provide a large sealing area for the sealing element 54 of the bodyside coupling member.

It will appreciated that the increased length of the inner wall 24 does not increase the profile height of the overall coupling, because the length can accommodated within the height of the bagside coupling member.

Figure 8:
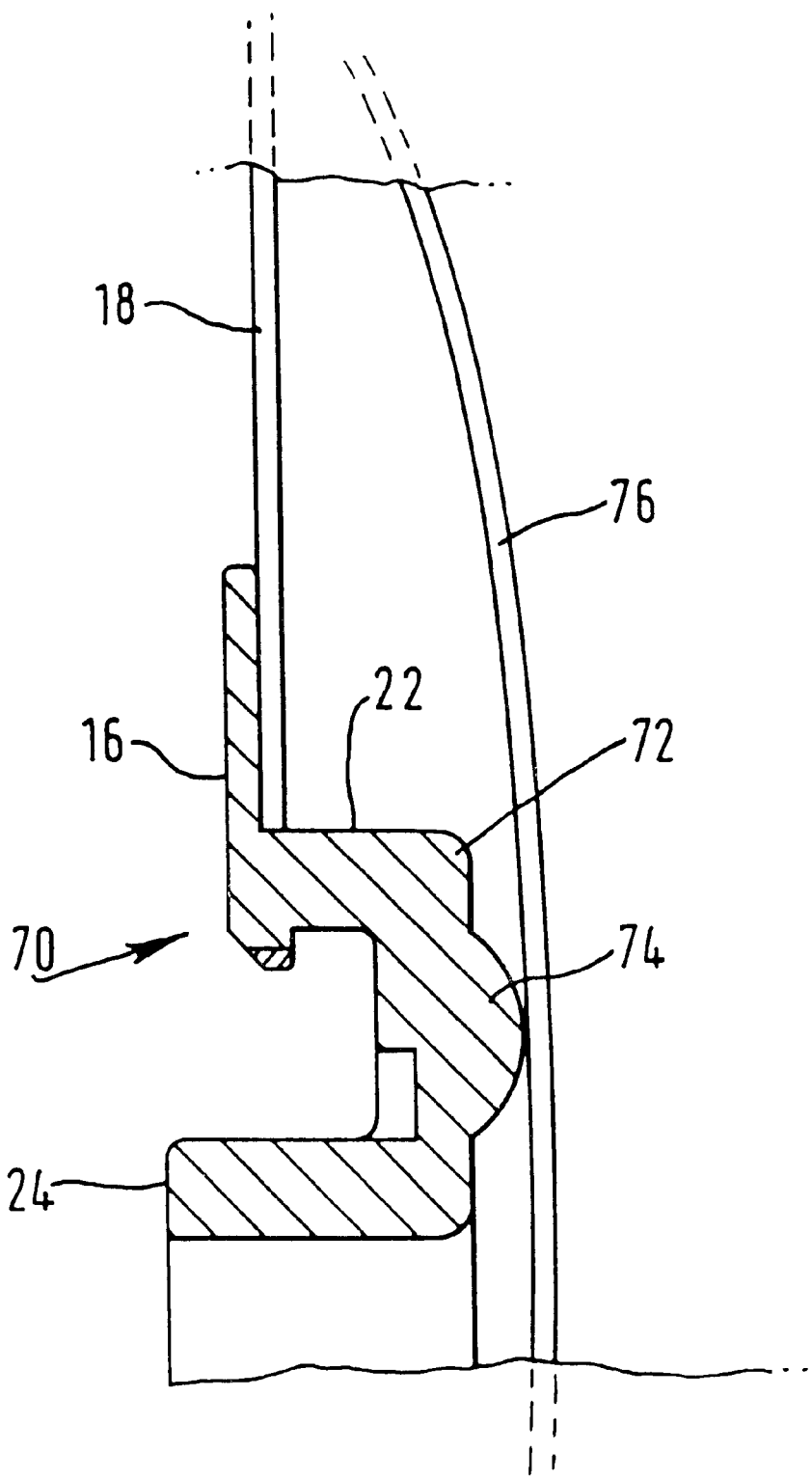
FIG. 8 is a partial schematic view showing the effect of the anti-stick projections of the bagside coupling member of FIG. 5.

(C) The coupling member 70 carries on its rear surface 72 a number of bump projections 74. As best seen in FIG. 8, the projections 74 serve two functions.

Firstly, the projections 74 act as an anti-sealing means to reduce any tendency for the plastics coupling member to stick to the rear wall 76 of the pouch. Such sticking is similar to the well-known problem of pouch pancaking, and might otherwise obstruct the passage of faecal matter through the bagside coupling member 70 and into the pouch. It is believed that the projections 74 (and the clearances between adjacent projections 74) considerably reduce the problem of sticking.

Secondly, the projections provide a tactile indication which the user can feel by finger through the pouch wall material. This can improve the extent to which a user is able to feel by hand the profile of the coupling member through the pouch wall material, to enable the user better to position his hands during fitting of the pouch to the body. It has been appreciated that the recessed nature of the bagside flush-fit coupling member results in the coupling being considerably more hidden for the user's view, and that this loss of visibility can make the coupling more difficult to fit and to remove. Therefore, the improved tactility of the coupling through the second pouch wall compensates for the loss of visibility of the coupling member.

It will be appreciated that any non-planar configuration of rear surface may be used to improve the tactility of the coupling through the pouch wall. It will also be appreciated that, additionally or alternatively, a non-stick coating may be applied to the rear surface 72 of the coupling 70, or to the confronting pouch wall 76 to provide or enhance the non-stick effect.

Figure 9:
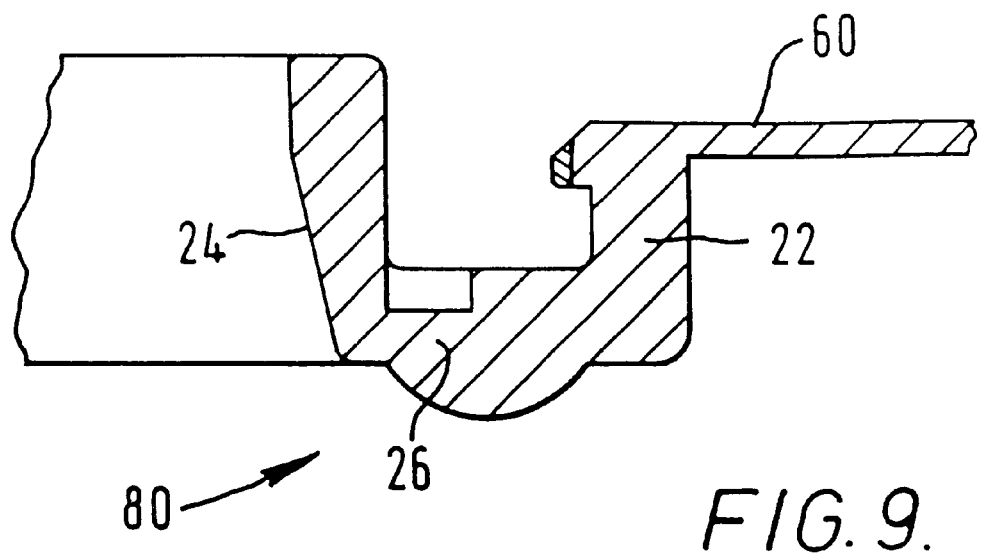
FIGS. 9 and 10 are partial schematic views showing the hinging effect in a further modified embodiment of bagside coupling member.
Figure 10:
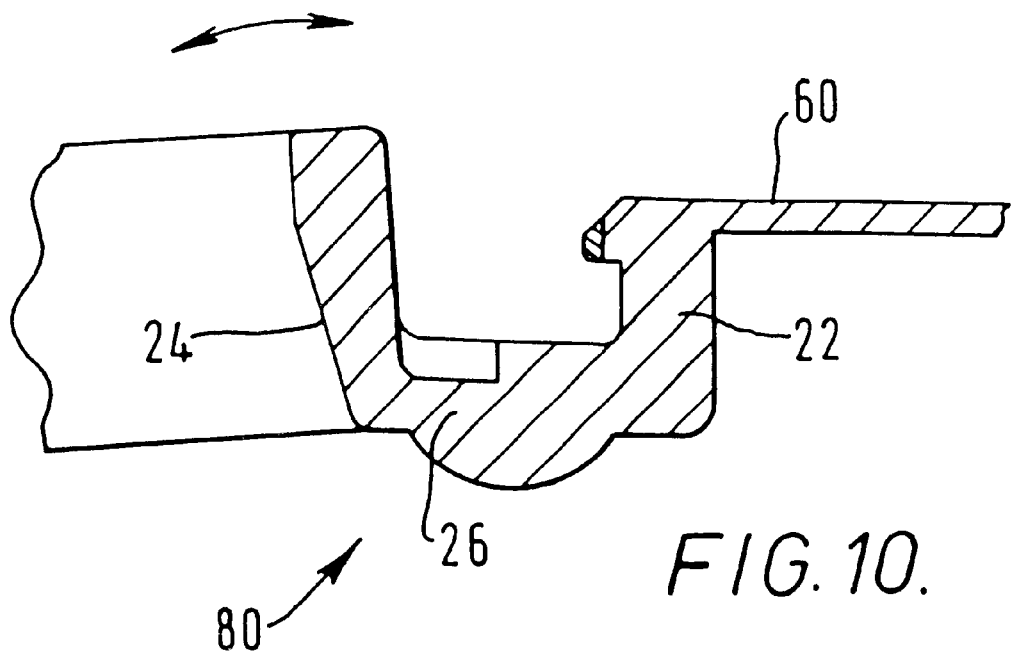
Figure 11:
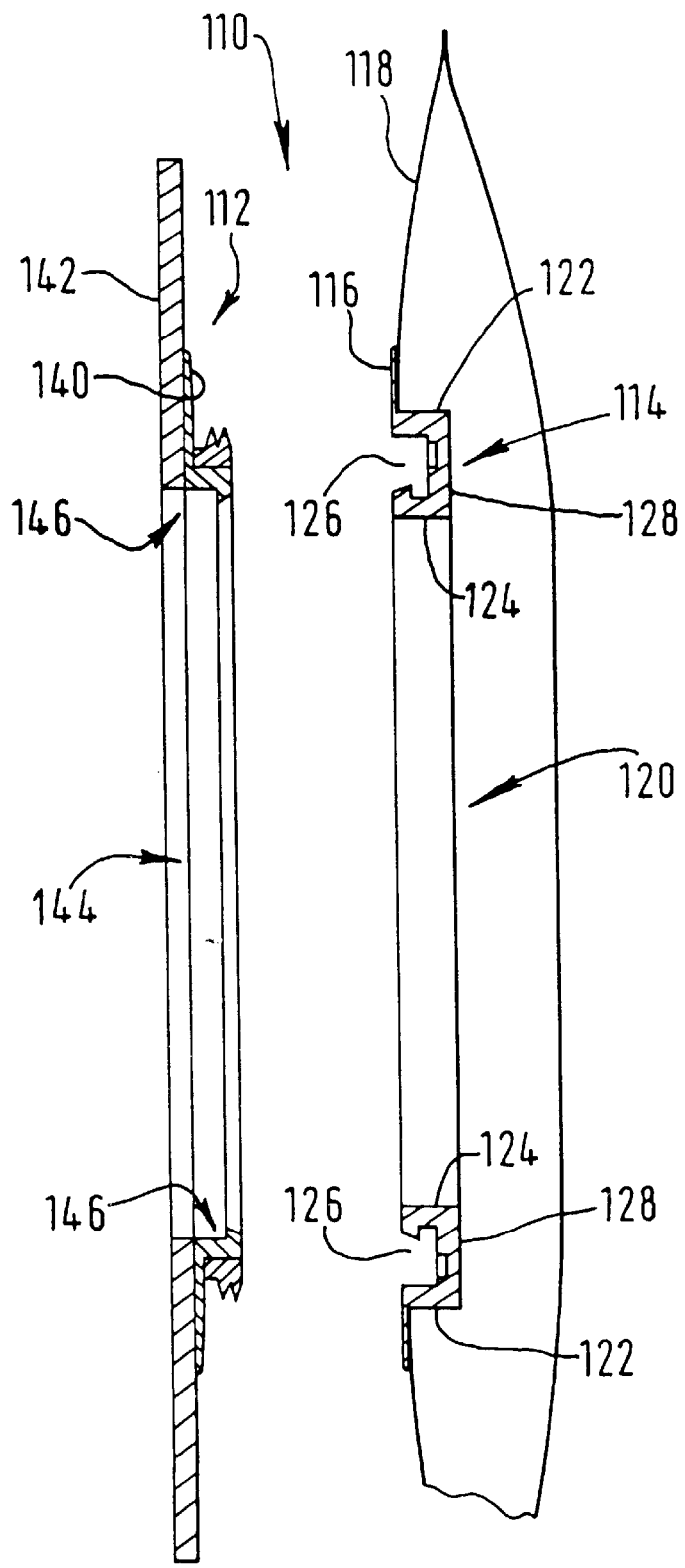
FIG. 11 is a schematic section view of a further embodiment of ostomy coupling.
Figure 12:
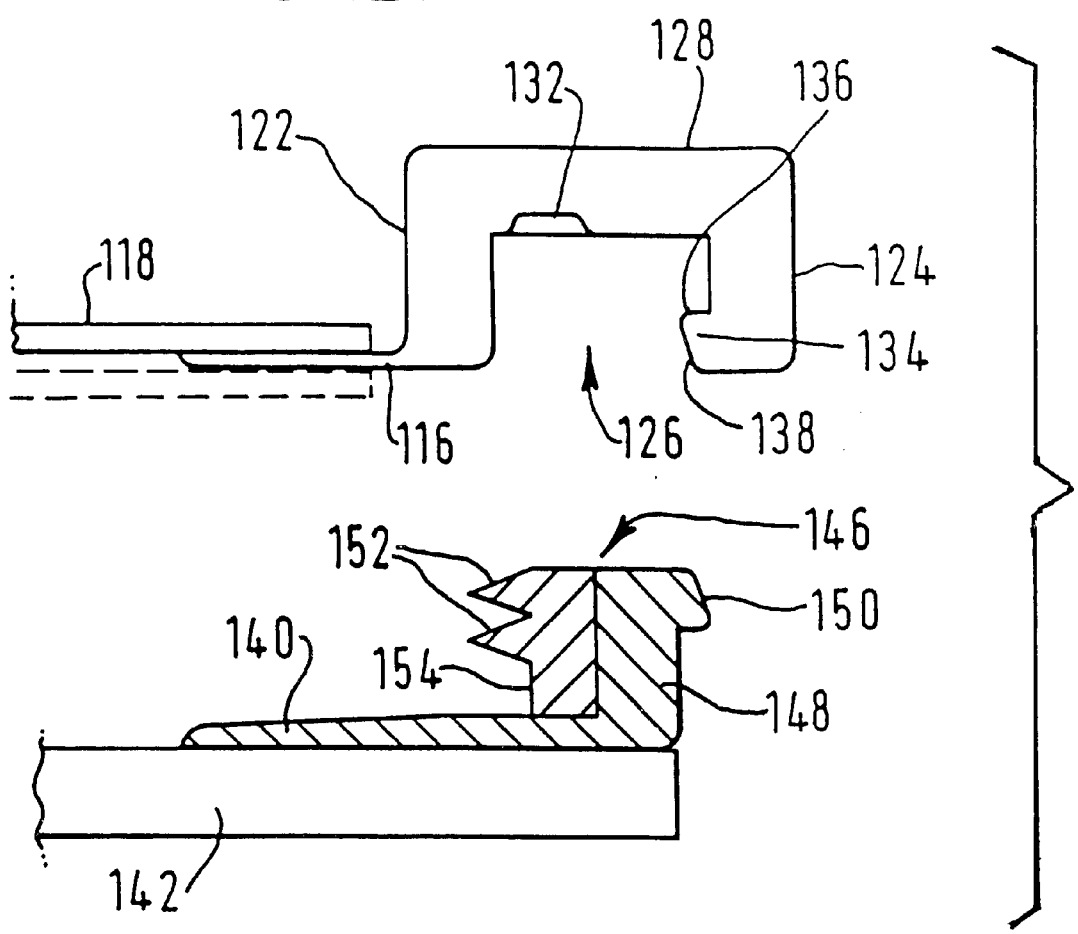
FIG. 12 is a partial schematic view of the coupling member in a disassembled condition.

FIGS. 9 and 10 illustrate a further modified embodiment of bagside coupling member 80. This is very similar to the bagside coupling member 70 illustrated in FIGS. 5 to 8, but in the present embodiment, the inner wall 24 tapers in thickness towards the junction with the channel floor 26. This reduced thickness provides a natural hinging effect to improve the ease with which the channel is able to open when flexed. This can address the problem of the channel tending to be stiff as a result of being supported by the flange 60 extending from the outer wall 22 around the channel mouth. Such stiffness might result in a high insertion force being required to assemble the bagside coupling member to the bodyside coupling member, and also a high peeling forced being required to separate the coupling members. By providing a natural hinging effect, the inner wall 24 is able to flex during assembly, and during peeling of the bagside coupling member, making the coupling easier to use without compromising the seal and security characteristics of the coupling.

Referring to FIGS. 11 to 14, a two-piece ostomy coupling 110 consists generally of a bodyside coupling member 112 and a bagside coupling member 114.

The bagside member 114 comprises a flange 116 which in this embodiment is attached to the outer face of a pouch wall 118 by gluing, welding, or any other suitable form of fixing. However, in a similar manner to the first embodiment and as explained further below, the flange 116 could be attached to the inner face of the wall 118 is desired. The flange 116 has a stomal aperture which is aligned with a corresponding aperture 120 in the pouch wall 118.

Depending from the inner edge of the flange 116 is an outer cylindrical wall 122 which extends rearwardly into the pouch, and positioned concentrically inside the outer wall 122 is a cylindrical inner wall 124. The inner wall 124 and the outer wall 122 define a channel 126, and are connected to each other by a channel floor 128.

A number of radially projecting belt tabs and/or pull tabs 130 are provided as extensions of the front flange 116, to enable the flange 116 to be gripped, as described later. The floor 128 of the channel 126 includes a plurality of, in this embodiment, regularly spaced, recesses 132 for facilitating moulding of the coupling member in the same manner as the recesses 30 in the first embodiment.

The inner wall 124 carries, on its outer face, a plurality of spaced apart projections 134. These serve to form an interlock with a corresponding formation of the bodyside coupling member 112. Each projection 134 includes a generally planar flat or undercut rear surface 136, and an upper ramp surface 138.

The bodyside member 112 comprises an annular flange 140 which is attached to an adhesive "wafer" or pad 142 for attachment to a person's skin. The pad 142 may be made of Stomadhesive or other known skin adhesives; such adhesives are well known to the skilled man and so are not described further here.

The flange 140 includes a stomal aperture 144 bounded by a generally annular formation 146 configured to fit within the channel 126 and including a first portion made of relatively hard plastics material, and a second portion made of a relatively soft plastics material. The first portion includes a generally cylindrical rib 148 which carries on its inner face a stepped or undercut locking formation 150 for co-operating with the projections 134.

The second portion comprises at least one (and in this embodiment two) generally radial sealing fins 152 which project radially outwardly from the rib 148. Each fin 152 extends from a base support region 154, and tapers towards its tip.

Figure 13:
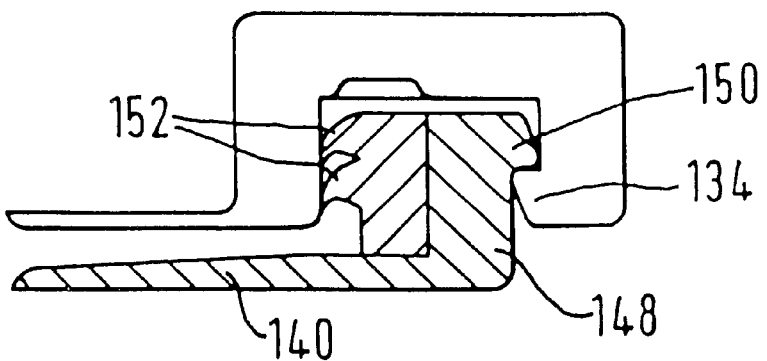
FIG. 13 is a partial schematic section showing the coupling member assembled together.

The fins 152 are dimensioned to be slightly "oversize" for fitting within the channel 126. Therefore, as best seen in FIG. 13, when the coupling members 112 and 114 are assembled, the tips of the fins 152 will engage against, and be deflected by, the inner surface of the outer channel wall 122. The bent tip of each fin 152 therefore engages the outer channel wall 122 over an axially spread cylindrical region, to increase the overall area of the seal. Such spreading of each seal over a cylindrical band can achieve much better seal performance than some other types of prior art low-profile seal which just tend to provide point sealing characteristics. In particular, the seal achieves the following advantages:

(a) the seal is able to withstand, without loss of integrity, movement and distortion of the coupling members 112 and 114 which inevitably occur in use when worn on the body;

(b) the seal deflects relatively easily so that it does not require a very great "insertion force" to assemble together the coupling members.

(c) the seal fins extend predominantly radially, so that the length of each seal fin does not compromise the "height" of the coupling members. Therefore, a very low coupling profile can be achieved. With the illustrated embodiment, a profile height of less than 5 mm can be achieved, preferably, as small as 4.4–4.5 mm or even less;

(d) the seal is able to accommodate tolerance variations in the sizes of either coupling member. This means that the coupling members do not have to manufactured to extremely precise manufacturing tolerances, and can lead in turn to cheaper production costs, and reduced reject products.

(e) the material for the sealing fins 152 can be chosen for optimum sealing characteristics without affecting the structural strength of the remainder of the coupling, or the security of the fastening between the two coupling members.

The tapering of each fin 152 ensures that any deflection of the fin 152 will occur predominantly at the tip, to achieve the desired cylindrical seal, rather than a point seal. The fins 152 are dimensioned to be slightly larger than the maximum envisaged channel size, bearing in mind the manufacturing tolerances of the coupling members.

Although in the illustrated embodiment, two sealing fins are illustrated, a single fin, or three or more fins may be used instead if desired. If more than one fin 152 is used, then in the present embodiment these project radially outwardly, for ease of moulding.

In this embodiment, the sealing fins 152 are of a different, softer material than the cylindrical rib 148. Convenient manufacturing techniques for producing the bodyside coupling member 112 of two materials include two shot moulding, and insert injection moulding. In the present embodiment, the base support region 154 provides additional contact area between the hard and soft materials to ensure that a firm integral connection is achieved during two shot moulding. Of course any suitable production technique including manual assembly of separate component parts, may be used as desired.

A suitable material for the rib 48 and the flange 140 is STD PVA Copolymer. A suitable material for the sealing fins 152 is synthetic rubber. Such materials can be chosen which bond chemically when two-shot moulded. If non-bonding materials are used, then a mechanical keying arrangement will need to be used.

Although it is preferred to use different materials for the sealing fins 152 and the rib 148, it will be appreciated that, if desired, the fins 152 and the rib 148 may be integrally moulded of the same material, for example, a flexible polymer.

Figure 14:
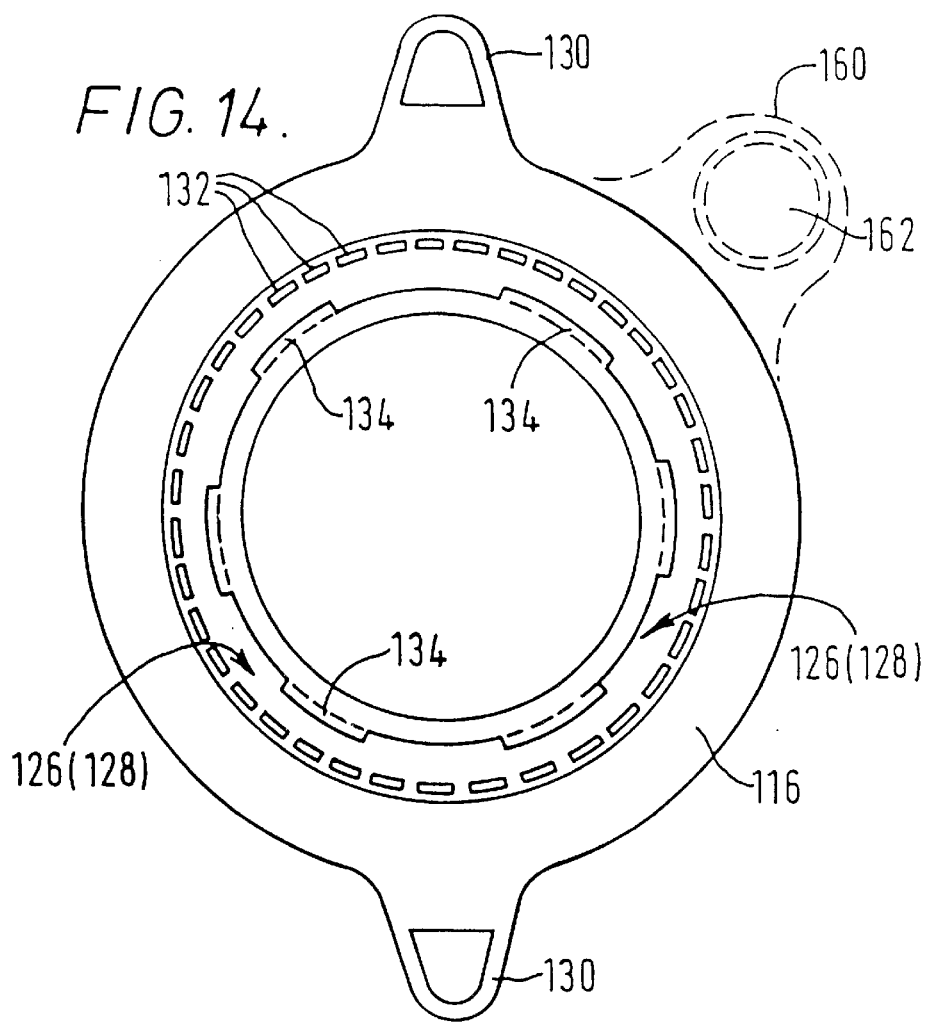
FIG. 14 is a front view of the bagside coupling member of FIG. 11.

As shown in phantom in FIG. 14, the flange 140 of the bagside coupling member 114 may carry an integral mounting 160 for a flatus filter (depicted schematically at 162). The mounting 160 may be in the form of an openable carrier to enable the filter 162 to be replaced, or it may be sealed closed. As illustrated, the mounting 160 is in the form of a lateral extension of the flange 140. However, it will be appreciated that the mounting 160 may take any suitable form, for example, a satellite coupled by webs to the flange 140, or be part of the flange 140. Such an integral filter assembly can provide additional advantages in terms of ease of manufacture, by providing self alignment of the filter, and also providing attachment of the filter and coupling member to the pouch in one welding step (rather than separate steps for the coupling member and for the filter).

In use, to assemble the coupling members 112 and 114, the formation 146 of the bodyside member 112 is pressed into the channel 126 of the bagside member 114. This requires only a modest insertion force. The locking formation 150 forms a snap fit with the projections 134 of the inner channel wall 124. As described above, the sealing fins 152 deflect to form a seal against the inner surface of the outer channel wall 122.

To separate the two coupling members, the user grips one of the belt tabs/pull tabs 30 and peels the bagside member 114 off the body side member 112. The bagside coupling member 114 is sufficiently flexible to enable the two coupling members to be separated with only a modest separation force being required. However, in normal use while being worn, the interlock between the locking formation 150 and the projections 134 maintains a secure fastening between the coupling members.

As in the first embodiment, the outer channel wall 122 and the inner channel wall 124 depend rearwardly from the front flange 116 of the bagside coupling member. The channel 126 is therefore "recessed" into the interior of the pouch. This can provide the impression of a very low profile coupling, because the pouch fits very closely to the adhesive pad 142, and the majority of the profile height of the coupling is concealed inside the pouch. If desired, any of the modification features illustrated in FIGS. 5–10 could also be included in the present embodiment.

It will of course be appreciated that in an alternative embodiment, the inner and outer channel walls 124 and 122 could if desired project forwardly from the flange 116, such that the flange is generally co-planar with the floor 128 of the channel 126.

In the illustrated embodiment, the flange 140 of the bagside coupling member 114 fits against the exterior face of the pouch wall. However, in an alternative embodiment, the bagside coupling member could be secured to the interior face of the pouch wall (as depicted in phantom in FIG. 12). Such an alternative arrangement could also use the integral filter mounting 160.

In the illustrated embodiment, the "female" coupling member 114 (with the channel 126) is on the bag-side, and the "male" coupling member 112 (with the projecting formation 146) is on the body side. This is because it is envisaged that the two-shot moulded male member will be slightly more expensive to produce than the single-shot moulded female member. In general the bagside member will be replaced more frequently than the bodyside member, and so it may be advantageous to use the cheaper coupling member as the more frequently replaced member. However, if desired, the male and female members may be interchanged so that the female member is on the body side, and the male member is on the bag side.

Figure 15:
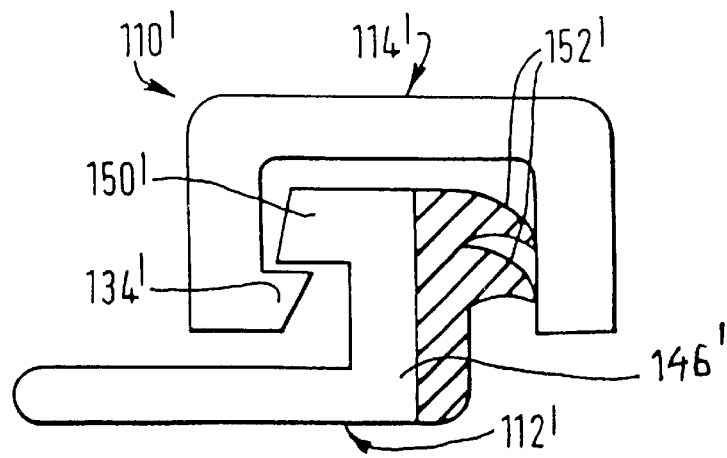
FIG. 15 is a partial schematic view of a modified embodiment of ostomy coupling.

FIG. 15 illustrates a modified embodiment of coupling 110'. This is similar to the first embodiment described above, and the same reference numerals are used where appropriate. The main difference in the second embodiment is that the sealing fins 152' project radially inwardly, and the locking formation 150' is on the radially outer edge of the formation 146'. The coupling functions in the same manner as the first embodiment, and can achieve the same reliable seal and low profile height as the first embodiment. However, at the current time, the first embodiment is preferred for ease of moulding.

Figure 16:
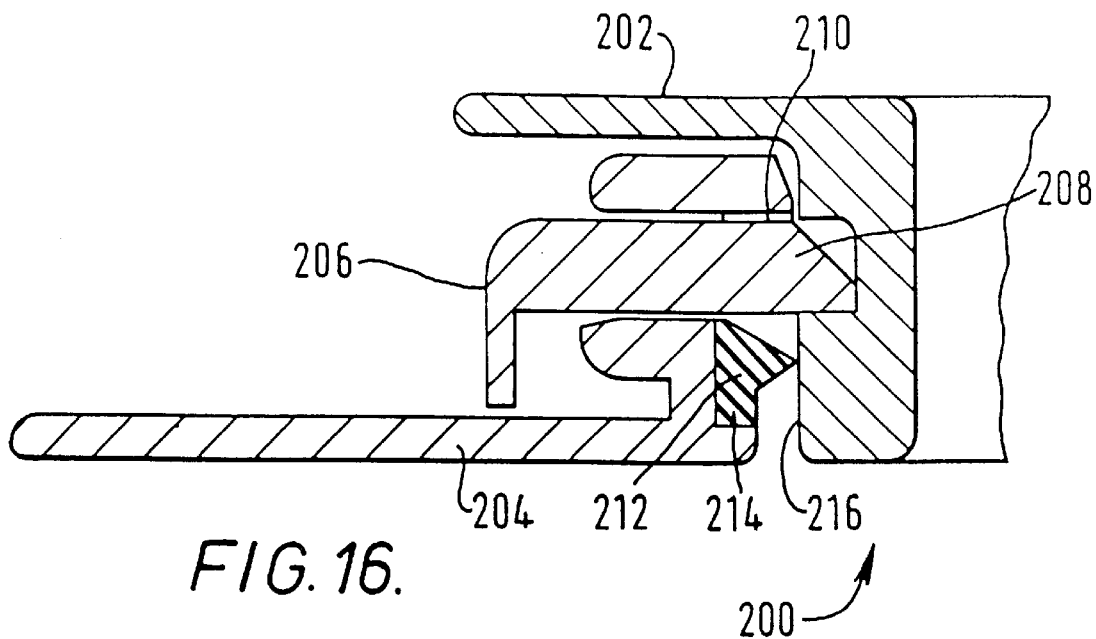
FIG. 16 is a partial schematic section through an embodiment of a three-piece ostomy coupling.

FIG. 16 illustrates a further embodiment of ostomy coupling 200, being a three piece coupling. The coupling consists of a bagside coupling member 202, and a bodyside coupling member 204 carrying a springy split locking ring 206. The function of the split locking ring is as described in GB-A-2299761 to which the reader is referred. Briefly, the locking ring 206 carries a number of locking tabs 208 which project through apertures 210 in the coupling member 204, to engage the bagside coupling member 202 to secure the two coupling members together. The upper edges of the tabs 208 are tapered to enable the bagside coupling member 202 to be inserted with a snap fit. To release the coupling members, the ring 206 is manipulated, e.g. moved angularly, causing the tabs to become withdrawn by a cam action against the edge surfaces (not shown) of the apertures 210. Once the tabs have been withdrawn radially, the bagside coupling member 202 can be separated from the bodyside member 204.

In this embodiment, the bodyside coupling member 204 carries a generally radial annular sealing fin 212 similar to the fins 152 described above. The fin 212 is of resilient plastics and is supported by a base 214 integrally moulded in a recess of the bodyside coupling member 204. The fin 212 tapes towards its tip, to form a resilient seal against a surface 216 of the bodyside coupling member 202 when the coupling members are assembled. The sealing fin can provide the same sealing characteristics and advantages as the fins 152 described above. Although only one sealing fin 212 is illustrated, a plurality of fins 212 may be used if desired.

Figure 17:
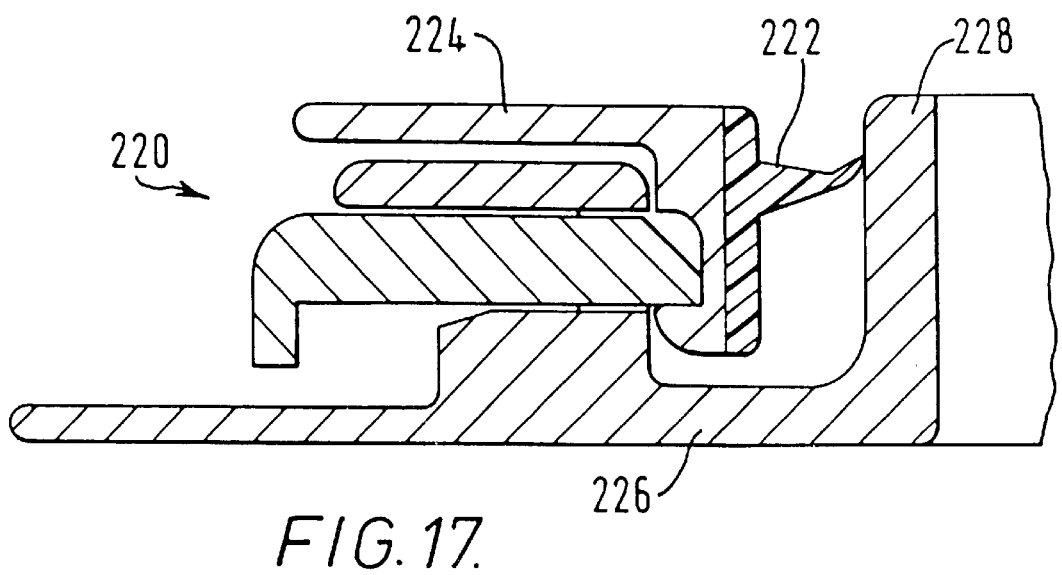
FIG. 17 is a partial schematic section through an alternative embodiment of three-piece ostomy coupling.

FIG. 17 illustrates a further embodiment of a three piece coupling 220 similar to the coupling 200 of FIG. 16. However, in the embodiment of FIG. 17, the sealing fin 222 is carried by the bagside coupling member 224. The bodyside coupling member 226 comprises an inner cylindrical wall 228 defining a channel in which the bagside coupling member 224 is received. The seal fin 222 bears against the inner cylindrical wall to form a resilient cylindrical band seal thereagainst. It will be appreciated that more than one seal fin 222 may be used as desired, although a single fin 222 illustrated in this embodiment for ease of moulding.

Figure 18:
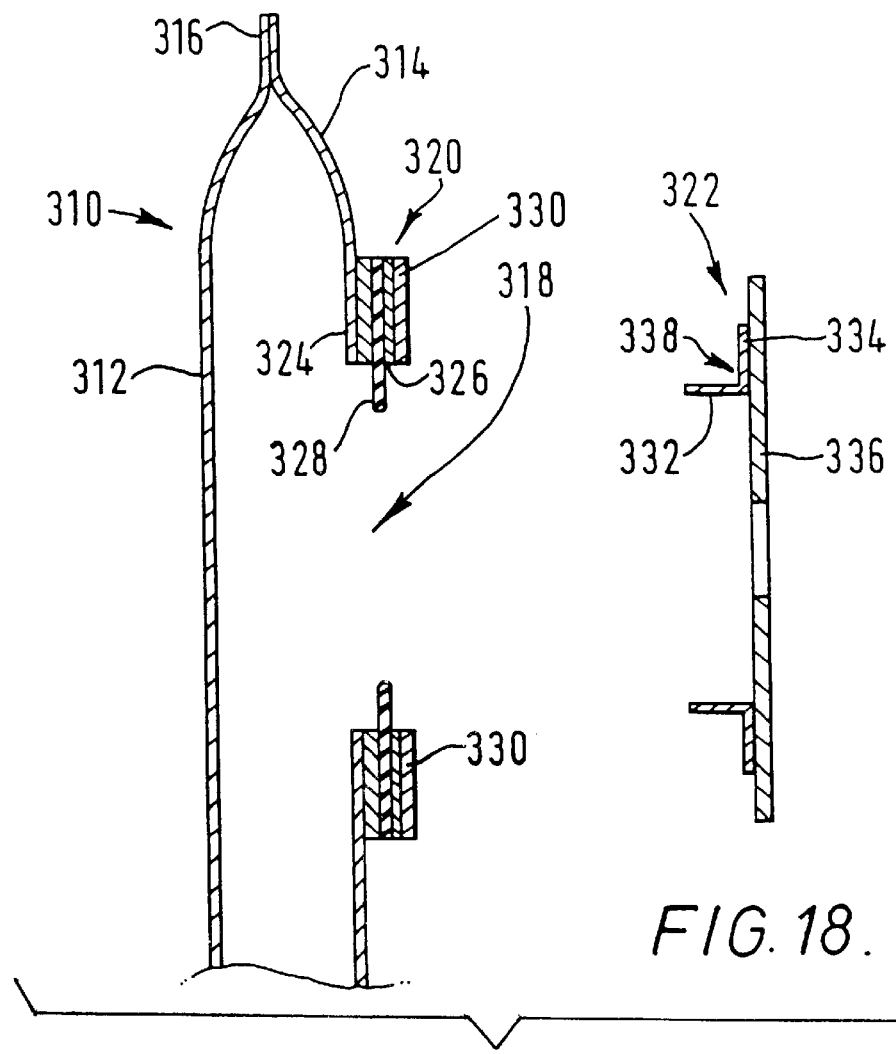
FIG. 18 is a partial schematic section showing an embodiment of an adhesive ostomy coupling.
Figure 19:
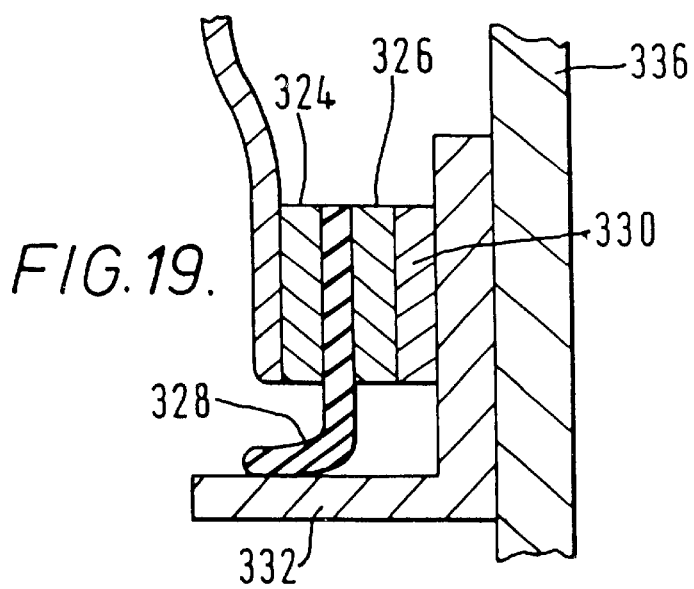
FIG. 19 is a partial schematic section showing the coupling members assembled together.

Referring to FIGS. 18 and 19, an ostomy pouch 310 includes a front wall 312 and a rear wall 314 of plastic film, welded together around a peripheral weld seam 316. The rear wall 314 of the pouch includes a stoma aperture 318 in which, typically, may be generally circular. Mounted around the stoma aperture 318 is a bag side coupling member which is releaseably attachable to a body side coupling member worn on the body.

The bag side coupling member 320 consists generally of a first annular member 324 secured to the rear wall 314 of the pouch, a second annular member 326, and an annular sealing diaphragm 328 sandwiched between the first and second annular members 324 and 326. The annular members 324 and 326 may be made, for example of plastics or of card, and the diaphragm 328 can be made of any soft, resiliently flexible material, such as rubber, soft rubber or a soft flexible thermoplastic elastomer.

The members 324, 326 and 328 can be secured together by any suitable means such as by adhesive, or by welding (if possible), or by a mechanical fastening or interlock.

The second annular member 326 carries a layer of adhesive 330 for allowing releasable attachment of the bag side coupling member 320 to the body side coupling member 322. The adhesive is preferably of a re-positionable type (also referred to as a "pealable and resealable" adhesive). Such adhesives are known to the skilled man.

The body side coupling member 322 comprises a generally cylindrical chute 332 from which projects a generally radial flange 334. The flange 334 is attached to a pad, or wafer 336 of skin compatible adhesive, such as stomadhesive, produced by Bristol-Myers Squibb company.

The flange 334 also serves to provide a seat surface 338 against which the adhesive 330 of the bag side coupling can adhere to hold the coupling members together when the bag side coupling member 320 is pressed onto the body side coupling member 322.

The chute 332 has an outer diameter which is smaller than the inner diameter of the annular members 324 and 326, so that the chute can be received within the annular members. However, the outer diameter of the chute 332 is greater than the inside diameter of the flexible diaphragm 328, such that the diaphragm 328 engages around the chute 332 to form a seal around the chute.

The sealing affect is illustrated in more detail in FIG. 19. As the bag side coupling member is advanced onto the body side member 322, the chute 332 forces the aperture in the diaphragm 328 to expand, and also causes the flexible diaphragm material to deflect in a direction towards the stoma aperture 318 in the pouch. The diaphragm material is easily flexible in order to accommodate such expansion and deflection, and thus forms a "stretched" fit around the chute 332. This can provide a reliable, generally gas-tight seal around the chute, with only a very modest "insertion" force being required to insert the chute through the diaphragm 328.

When the bag-side member 320 is removed from the body side member, the chute 332 is able to slide out easily from the aperture in the sealing diaphragm 328, and the sealing diaphragm 328 can return to its normal, planar shape under it's own resilience.

Figure 20:
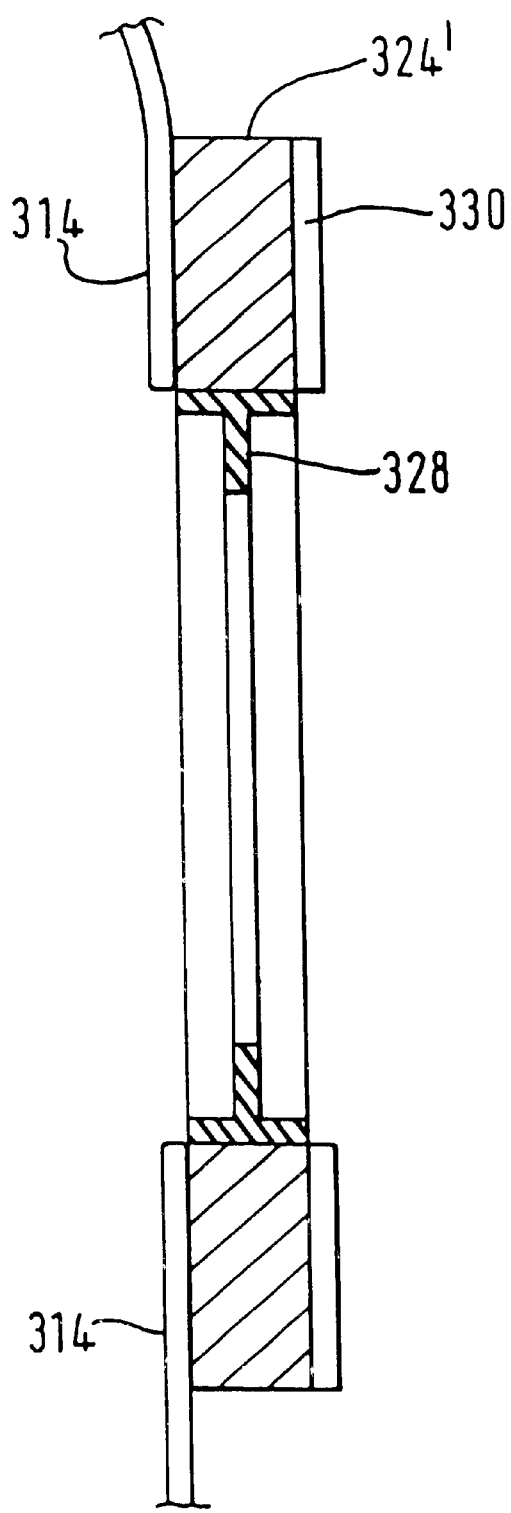
FIG. 20 is a section through a modified embodiment of bagside coupling member.

FIG. 20 shows a modified form bag side coupling member 320. In this modified embodiment, the annular members 324 and 326 are formed as a single, annular member 324'. The flexible diaphragm 328 of resilient material is integrally moulded with the annular member 324', for example using two-shot moulding, or insert injection moulding. This can enable can intregal coupling member to be formed of two plastics materials.

As illustrated, the coupling member 324' carries the adhesive layer 330 in the same manner as illustrated in FIG. 18.

In a yet further form of this coupling member, the coupling member could be intregally moulded for a single, flexible, plastics material, for example, a flexible thermoplastic elastomer.

FIG. 21 illustrates a further embodiment of ostomy coupling. This is similar to the embodiment illustrated in FIG. 20, but differs in that the sealing fin 366 is carried on the male coupling member, rather than on the female coupling member.

The sealing fin projects generally radially from a supporting portion 372 of the same material as the fin 366. The supporting portion 372 is intregally moulded with the remainder of the male coupling member, by using a two-shot moulding process (or an insert injection moulding process), and the supporting portion 372 serves to provide sufficient contact area between the two materials to ensure reliable bonding during moulding.

The flexible fin 366 has a larger outer diameter than the inner diameter of the female coupling member 380, to form a resilient seal therewith when the coupling members are assembled together.

Although the coupling members of the preferred embodiment are generally circular, it will be appreciated that other closed-loop shapes may be used instead if desired.

It will be appreciated that the foregoing description is merely illustrative of preferred forms of the invention, and that many modifications may be made within the scope and/or principles of the invention. Features believed to be of particular importance are defined in the appended claims. However, the Applicant claims protection for any novel feature or idea described herein and/or illustrated in the drawings, whether or not emphasis has been placed thereon.

What is claimed is:

1. A flush fit ostomy coupling, comprising:
    a bagside coupling member comprising an inner wall and an outer wall defining a channel therebetween, a mounting flange extending outwardly from the outer wall at a point remote from the channel floor; and
    a bodyside coupling member comprising a projection which, in use, is received within the channel of the bagside coupling member for interlocking engagement therewith;
    wherein the bagside coupling member comprises anti-stick means on the rear of the channel floor.

2. The coupling according to claim 1, wherein the anti-stick means comprises a coating of anti-stick material.

3. The coupling according to claim 1, wherein the anti-stick means comprises a non-planar region.

4. The coupling according to any of claim 1, wherein the rear surface of the channel floor is substantially non-planar.

5. A flush fit ostomy coupling, comprising:
    a bagside coupling member comprising an inner wall and an outer wall defining a channel therebetween, a mounting flange extending outwardly from the outer wall at a point remote from the channel floor; and
    a bodyside coupling member comprising a projection which, in use, is received within the channel of the bagside coupling member for interlocking engagement therewith;
    wherein the rear surface of the channel floor is substantially non-planar.

6. A coupling according to claim 5, comprising a plurality of projections on the rear of the channel floor.

7. A bagside coupling member for a flush fit ostomy coupling, for coupling to a bodyside coupling member, the bagside coupling member comprising:
    generally concentric inner and outer walls defining a channel therebetween;
    a securing flange extending generally radially outwardly from a point removed from the channel floor; and
    anti-stick means on the rear of the channel floor.

8. A coupling member according to claim 7, wherein the anti-stick means comprises a coating of anti-stick material.

9. A coupling member according to claim 7, wherein the anti-stick means comprises a non-planar region.

10. A coupling member according to claim 7, wherein the rear surface of the channel floor is substantially non-planar.

11. A bagside coupling member for a flush fit ostomy coupling, for coupling to a bodyside coupling member, the bagside coupling member comprising:
    generally concentric inner and outer walls defining a channel therebetween;
    a securing flange extending generally radially outwardly from a point removed from the channel floor;
    wherein the rear surface of the channel floor is substantially non-planar.

12. A bagside coupling member according to claim 11, comprising a plurality of projections on the rear of the channel floor.

* * * * *